US007427766B2

(12) United States Patent
Jonkers et al.

(10) Patent No.: US 7,427,766 B2
(45) Date of Patent: Sep. 23, 2008

(54) METHOD AND APPARATUS FOR PRODUCING EXTREME ULTRAVIOLET RADIATION OR SOFT X-RAY RADIATION

(75) Inventors: Jeroen Jonkers, Aachen (DE); Dominik Marcel Vaudrevange, Aachen (DE); Willi Neff, Kelmis (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 246 days.

(21) Appl. No.: 10/570,535

(22) PCT Filed: Sep. 1, 2004

(86) PCT No.: PCT/IB2004/051651

§ 371 (c)(1), (2), (4) Date: Mar. 3, 2006

(87) PCT Pub. No.: WO2005/025280

PCT Pub. Date: Mar. 17, 2005

(65) Prior Publication Data

US 2007/0090304 A1 Apr. 26, 2007

(30) Foreign Application Priority Data

Sep. 11, 2003 (DE) ................................ 103 42 239

(51) Int. Cl.
*A61N 5/06* (2006.01)
*G01J 3/10* (2006.01)
*H05G 2/00* (2006.01)

(52) U.S. Cl. .............................. 250/504 R; 250/503.1; 250/493.1; 372/76; 315/111.21

(58) Field of Classification Search ............ 250/504 R, 250/503.1, 493.1; 372/76; 315/111.21
See application file for complete search history.

(56) References Cited

U.S. PATENT DOCUMENTS 6,320,937 B1 * 11/2001 Mochizuki .................. 378/143

FOREIGN PATENT DOCUMENTS

WO WO199929145 6/1999
WO WO200101736 1/2001

* cited by examiner

*Primary Examiner*—Nikita Wells
*Assistant Examiner*—Meenakshi S Sahu

(57) ABSTRACT

A method of producing extreme ultraviolet radiation (EUV) or soft X-ray radiation by means of an electrically operated discharge, in particular for EUV lithography or for metrology, in which a plasma (22) is ignited in a gaseous medium between at least two electrodes (14, 16) in a discharge space (12), said plasma emitting said radiation that is to be produced. The gaseous medium is produced from a metal melt (24), which is applied to a surface in said discharge space (12) and at least partially evaporated by an energy beam, in particular by a laser beam (20).

26 Claims, 7 Drawing Sheets

METHOD AND APPARATUS FOR PRODUCING EXTREME ULTRAVIOLET RADIATION OR SOFT X-RAY RADIATION

The invention relates to a method and an apparatus for producing extreme ultraviolet radiation (EUV) or soft X-ray radiation by means of an electrically operated discharge, in particular for EUV lithography or for metrology, in which a plasma is ignited in a gaseous medium between at least two electrodes in a discharge space, said plasma emitting said radiation that is to be produced.

Preferred fields of application of the invention described below are those which require extreme ultraviolet radiation (EUV) or soft X-ray radiation having a wavelength in the region of around 1 nm-20 nm, such as, in particular, EUV lithography or metrology.

The invention relates to gas-discharge-based radiation sources in which a hot plasma is produced by a pulsed current of an electrode system, said plasma being a source of EUV or soft X-ray radiation.

The prior art is essentially described in the documents PCT/EP98/07829 and PCT/EP00/06080.

The prior art in respect of an EUV source is shown schematically in FIG. 8. The gas discharge radiation source generally consists of an electrode system consisting of anode A and cathode K, which is connected to a current pulse generator, symbolized in the figure by the capacitor bank $K_0$. The electrode system is characterized in that the anode A and cathode K each have boreholes as openings. Without restricting the general nature of the figure, the anode A is the electrode facing the application. The electrode system is filled with a discharge gas at pressures in the range of typically 1 Pa-100 Pa. By virtue of a pulsed current of typically a few tens of kA to at most 100 kA and pulse durations of typically a few tens of ns to a few hundred ns, a pinch plasma is produced in the gap between anode A and cathode K, which pinch plasma, by means of heating and compression by the pulsed current, is brought to temperatures (a few tens of eV) and densities such that it emits characteristic radiation of the working gas used in the spectral range of interest. The charge carriers needed to form a low-resistance channel in the electrode gap are produced in the rear space (hollow electrode), as shown in FIG. 8 in the hollow cathode K. The charge carriers, preferably electrons, may be produced in various ways. As examples, mention may be made of the production of electrons by surface discharge triggers, a high dielectric trigger, a ferroelectric trigger, or else by prior ionization of the plasma in the hollow electrode K.

The electrode system is situated in a gas atmosphere having typical pressures in the range 1 Pa-100 Pa. Gas pressure and geometry of the electrodes are selected such that the ignition of the plasma takes place on the left branch of the Paschen curve. The ignition then takes place in the region of the long electrical field lines, which occur in the region of the boreholes. A number of phases can be distinguished during discharge. Firstly, ionization of the gas along the field lines in the borehole region. This phase creates the conditions for forming a plasma in the hollow cathode K (hollow cathode plasma). This plasma then leads to a low resistance channel in the electrode gap. A pulsed current is sent via this channel, which pulsed current is generated by the discharging of electrically stored energy in a capacitor bank $K_0$. The current leads to compression and heating of the plasma, so that conditions are obtained for the efficient emission of characteristic radiation of the discharge gas used in the EUV range.

One essential property of this principle is that there is in principle no need for a switching element between the electrode system and the capacitor bank. This allows a low inductive, effective coupling-in of the electrically stored energy. Pulse energies in the region of a few Joules are thus sufficient to generate the necessary current pulses in the region of several kiloamperes to a few tens of kiloamperes. The discharge may thus advantageously be operated in self-breakdown, that is to say the capacitor bank $K_0$ connected to the electrode system is charged up to the ignition voltage which is determined by the conditions in the electrode system. By means of secondary electrodes it is moreover possible to influence the ignition voltage and as a result define the time of discharge. As an alternative, it is also possible to charge the capacitor bank $K_0$ only up to below the ignition voltage and to trigger the gas discharge by active measures (triggering) which produce a plasma in the hollow cathode.

One significant disadvantage of gas discharge sources according to the prior art is the fact that only gaseous substances can be used as discharge gas. As a result, there may be significant limitations in respect of the wavelengths that can be produced in the source, since the radiation properties depend on the highly ionized charge states of the respective element. In respect of EUV lithography, however, the radiation of, for example, lithium or tin would be of interest in particular. One expansion in this respect is given by an application by Philips relating to the use of halides, according to which halogen compounds having a low boiling point are brought into the gaseous state by heating and are introduced into the electrode system. Although the favorable spectral properties of the source are thereby obtained, only a relatively low conversion efficiency of electrical energy into usable radiation energy is achieved on account of the high proportion of halogens. In order to achieve a necessary radiation power, therefore, very high electrical powers have to be fed into the source, and this leads to high electrode wear. This wear leads to a low service life of the light source. In order to increase the service life, a system is proposed where the entire electrode system together with the electrical power supply rotates in order that each electrical pulse acts in an offset manner on a fresh surface of the electrodes. One great technical disadvantage of this concept is, for example, the fact that the electrodes together with the cooling and the entire power supply have to be introduced into a vacuum system using a lead-through which allows rotary movements.

It is therefore an object of the invention to provide a method of the above mentioned type which is free of the disadvantages of the prior art and at the same time allows greater radiation power without high electrode wear.

According to the invention, this object is achieved in a method of the type mentioned above wherein the gaseous medium used as discharge gas is produced from a metal melt, which is applied to a surface in the discharge space and at least partially evaporated by an energy beam. This energy beam can be, for example, an ion beam, an electron beam or a laser beam. Preferably, a laser beam is used for evaporation of the metal melt on said surface.

Said surface preferably is the surface of a component which is in the vicinity of a region between the two electrodes where the plasma is ignited. Preferably this surface is the outer surface of the electrodes or the surface of an optional metal screen arranged between the two electrodes.

A main aspect of the invention, therefore, consists in the use of a metal melt which is applied to a surface in the discharge space and which distributes there in a layer-like manner. The metal melt on this surface is evaporated by an energy beam. The resulting metal vapor forms the gaseous medium for the plasma generation.

In order for the metal melt to distribute even better on said surface, in particular on the outer surface of the electrodes or on the surface of the metal screen, it is advantageous to place the electrodes and/or the metal screen in rotation during operation.

In one embodiment the rotation axes of the electrodes are inclined to one another. In this case even with plate like electrodes a region for plasma ignition is defined in which the electrodes are spaced at the smallest distance from one another.

There are many possibilities for applying the metal melt from outside to said surface, in particular to the surface of the electrodes and/or to the surface of the metal screen. This may take place, for example, by means of feed lines, the openings of which are arranged close to the respective surface. It is particularly advantageous, however, if the electrodes or the metal screen or both dip, while rotating, into containers containing the metal melt in order to receive the metal melt.

According to one embodiment of the invention, it is provided that the layer thickness of the metal melt applied to the surface of the electrodes and/or to the surface of the metal screen is set. In this case, it is advantageous to set the layer thickness to a range of 0.5 μm to 40 μm.

By virtue of the intimate contact of the electrodes and/or the metal screen with the metal melt, in particular in the case of a rotating movement while dipping into a container with the metal melt, it is possible for the heated electrodes as well as for the heated metal screen to be able to give off their energy efficiently to the metal melt. The rotating electrodes then require no separate cooling. However, it is then advantageous if the temperature of the metal melt is set.

The rotation speed of the electrodes or of the metal screen is preferably set so high that two consecutive pulses of the energy beam do not overlap on the surface of these components.

There is a very low electrical resistance between the electrodes and the metal melt. It is therefore advantageous if the two electrodes are supplied with power via the metal melt.

It is furthermore advantageous if the plasma is produced in a vacuum chamber which is evacuated before starting the evaporation process.

During production of the plasma, it is possible that some of the electrode material is evaporated and condenses at different points of the electrode system. It is then advantageous if this metal vapor is prevented from escaping.

It is furthermore advantageous if the electrodes are placed at a definable potential relative to the housing of the vacuum chamber. This allows on the one hand an improved power supply and use of power. On the other hand this may also serve to prevent the metal vapor from escaping.

In order to achieve a more uniform radiation intensity in case of a laser beam as an energy beam, it is advantageous if the laser beam is transmitted by a glass fiber.

If the laser beam is directed onto the region via a mirror, soiling of the optics used for laser radiation can more effectively be reduced or can prevented. The use of a mirror also allows to couple in the laser beam from a side opposed to the side on which the produced EUV radiation or soft X-ray radiation is coupled out.

According to a further advantageous embodiment of the invention, it is provided that the energy beam is distributed over a number of points or a circular ring.

In order to prevent the vapor produced from condensing on the housing inner wall, it is advantageous if the electrodes are screened by metal.

In many applications it is desirable to be able to freely select the outcoupling location of the EUV radiation, at least within certain limits. For this, it is advantageous if the orientation of the rotation axes of the electrodes, which preferably are inclined to one another, is changed in order to set the outcoupling location of the radiation.

In order to be able to ensure the quality of the radiation produced, it is advantageous if the radiation produced is detected by means of a detector, the output value of which controls or switches off the production process.

It is furthermore an object of the invention to provide an apparatus of the above mentioned type which is free of the disadvantages of the prior art and at the same time allows greater radiation power without high electrode wear.

According to the invention, this object is achieved in an apparatus of the type mentioned above comprising a device for applying a metal melt to a surface in said discharge space and an energy beam device adapted to direct onto said surface an energy beam evaporating said applied metal melt at least partially thereby producing the gaseous medium used as discharge gas.

Since the advantages of the embodiments of the apparatus specified in the dependent claims are essentially the same as those of the method according to the invention, a detailed description of these dependent claims is not given.

The invention will be further described with reference to exemplary embodiments shown in the drawings to which, however, the invention is not restricted. Also any reference signs in the description or in the claims do not limit the scope of protection to these special embodiments.

Figure 6A:
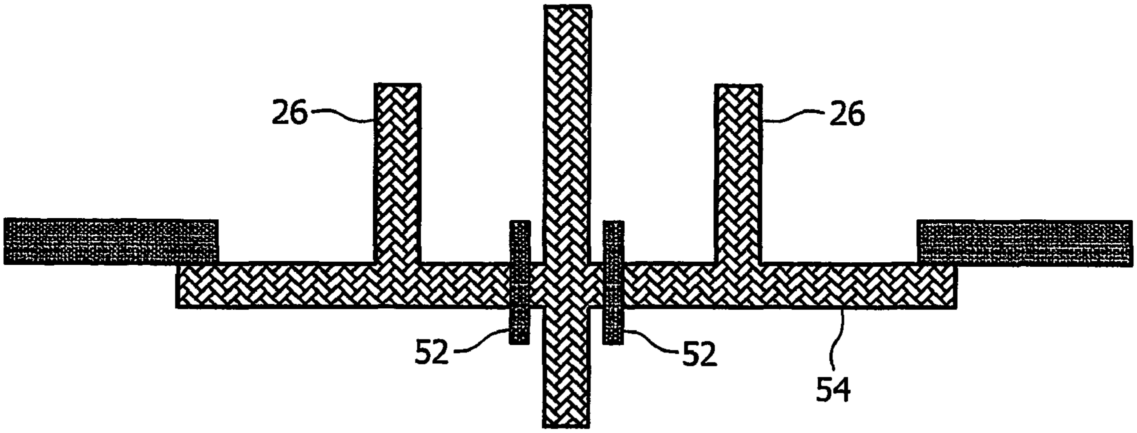
Figure 6B:
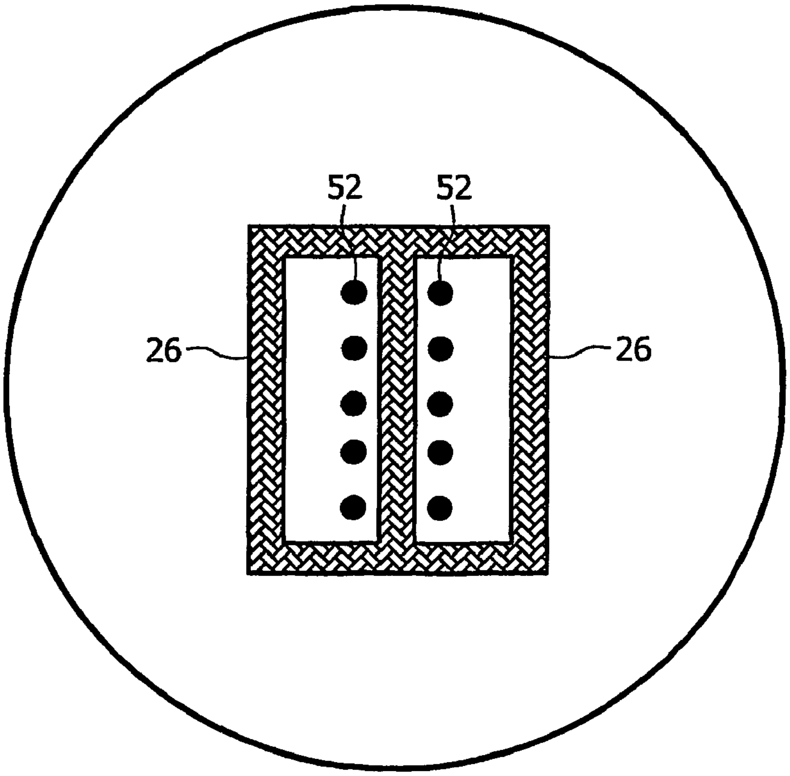

FIGS. 6*a, b* show schematic diagrams of a container for metal melt in side view and in plan view.

Figure 7:
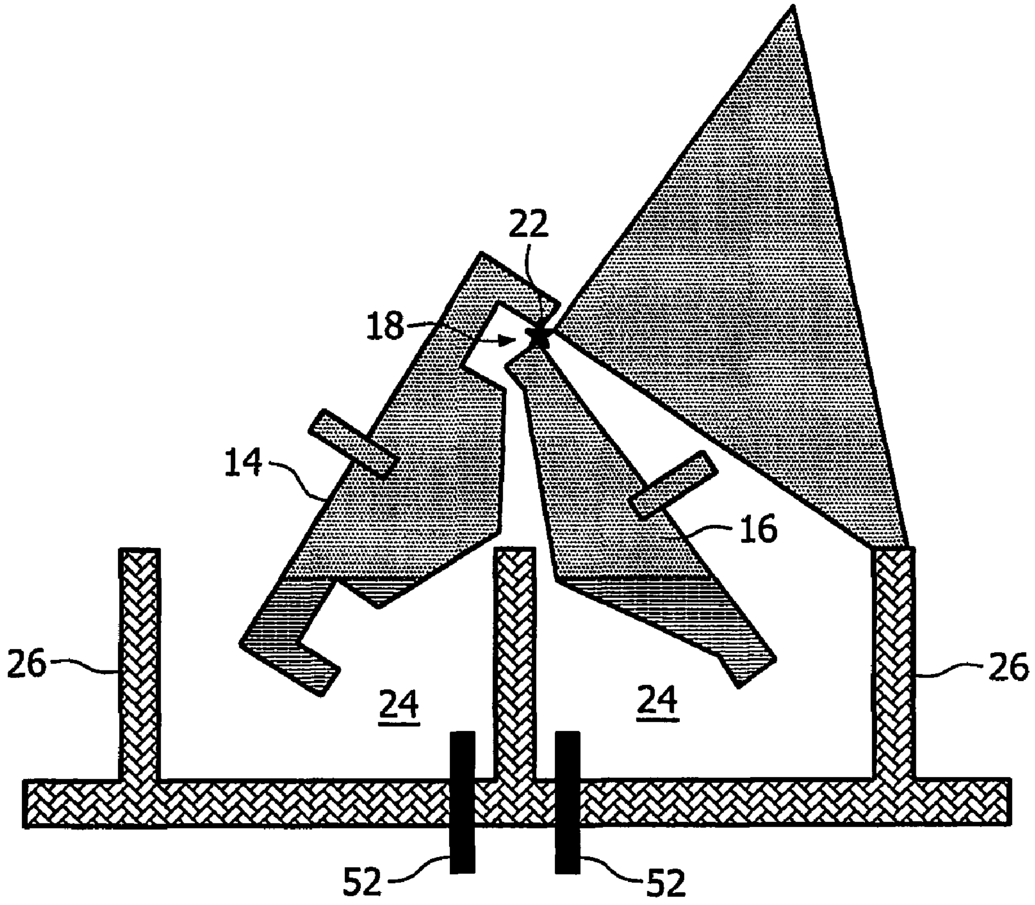

FIG. 7 shows a schematic and partially cut-away diagram of electrodes of a further embodiment.

Figure 8:
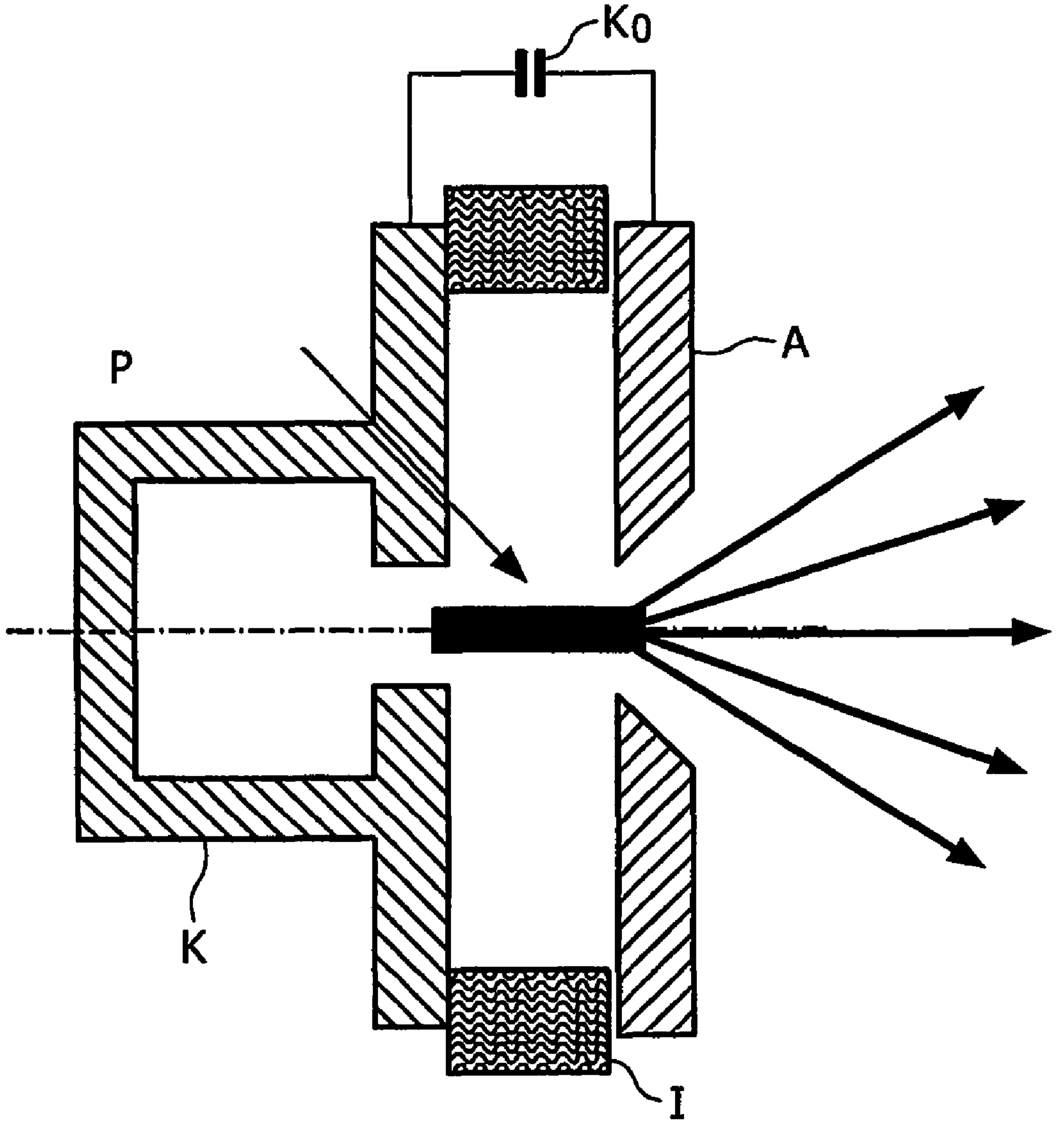
Prior Art FIG. 8

FIG. 8 shows a partially cut-away side view of an apparatus for producing EUV radiation according to the prior art.

Figure 9:
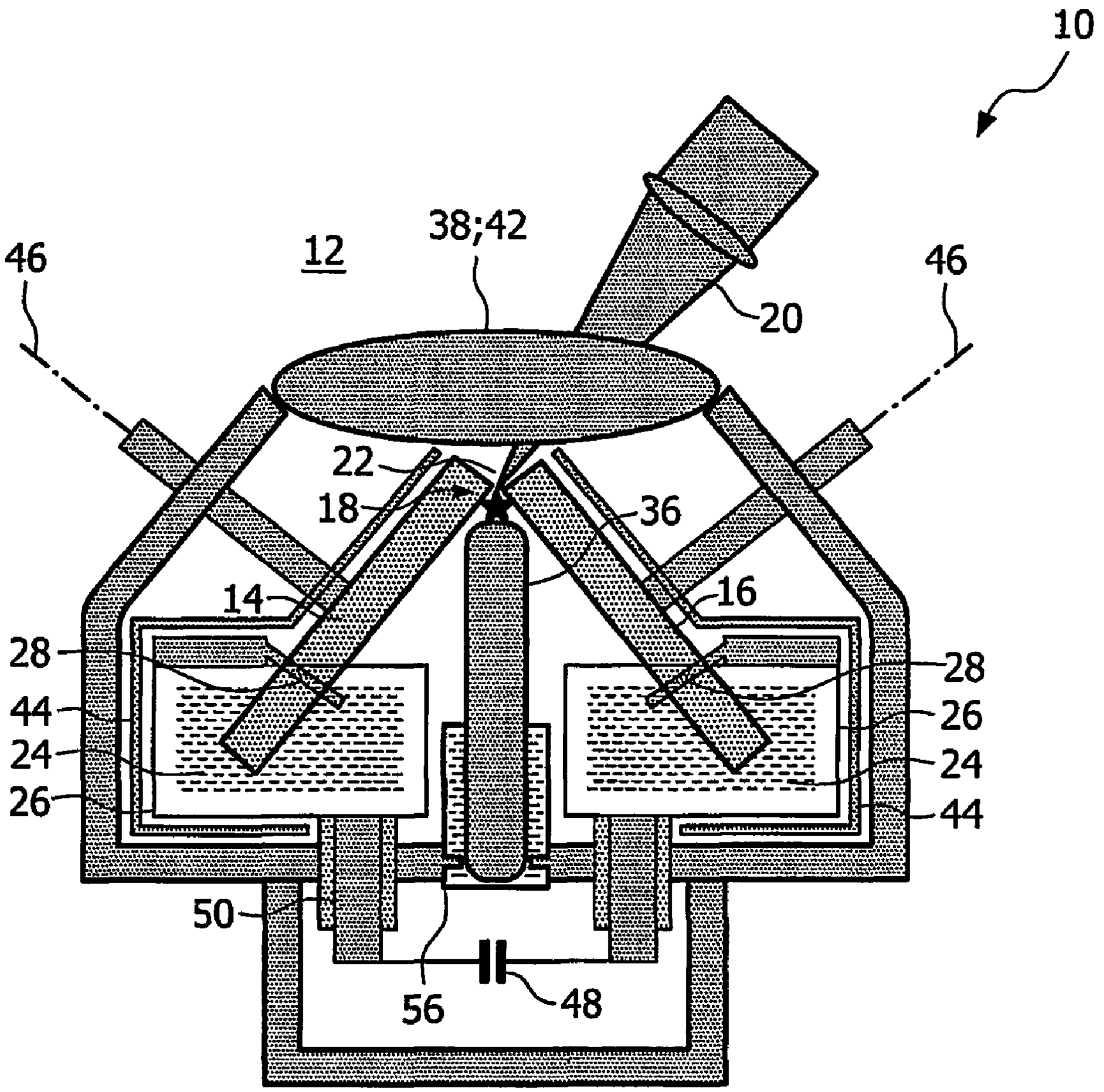

FIG. 9 shows a schematic, partially cut-away side view of the apparatus according to a further embodiment.

A number of examples of embodiments of an apparatus 10 for producing extreme ultraviolet radiation (EUV) or soft X-ray radiation by means of an electrically operated discharge will now be described with reference to FIGS. 1 to 7. This EUV is used in particular in EUV lithography or in metrology.

The apparatus 10 has first and second electrodes 14 and 16 arranged in a discharge space 12 of predefinable gas pressure. These electrodes 14 and 16 are at a small distance from one another at a predefinable region 18.

A laser source, not shown in any more detail, generates a laser beam 20 which is directed onto a surface in the region 18 in order to evaporate a supplied medium in this region 18. The resulting vapor is ignited to form a plasma 22. The medium used in this case consists of a metal melt 24 which is applied to the outer surface of the electrodes 14, 16. In all examples of embodiments, this is effected in that it is possible for the electrodes 14, 16 to be placed in rotation during operation and to dip, while rotating, into containers 26 containing metal melt 24 in order to receive the metal melt 24.

Furthermore, there is a device 28 for setting the layer thickness of the metal melt 24 that can be applied to the two electrodes 14, 16. Of course, there are a large number of possibilities for this, wherein in this case strippers 28 are used as the device, said strippers in each case reaching up to the outer edge of the corresponding electrodes 14, 16. There are also means 30 for setting the temperature of the metal melt 24. This takes place either by a heating device 30 or by a cooling device 30.

In the examples of the embodiments shown, the power for the electrodes 14, 16 is supplied via the metal melt 24. This is realized by connecting a capacitor bank 48 via an insulated feed line 50 to the respective containers 26 for the metal melt 24.

In order that the EUV can be produced in vacuum, the apparatus is provided with a housing.

For better intensity distribution of the laser beam 20, the latter is transmitted via a glass fiber (not shown). In order that the optics required for this is even better protected, the laser beam 20 is deflected onto the region 18 via a mirror 34.

Figure 1:
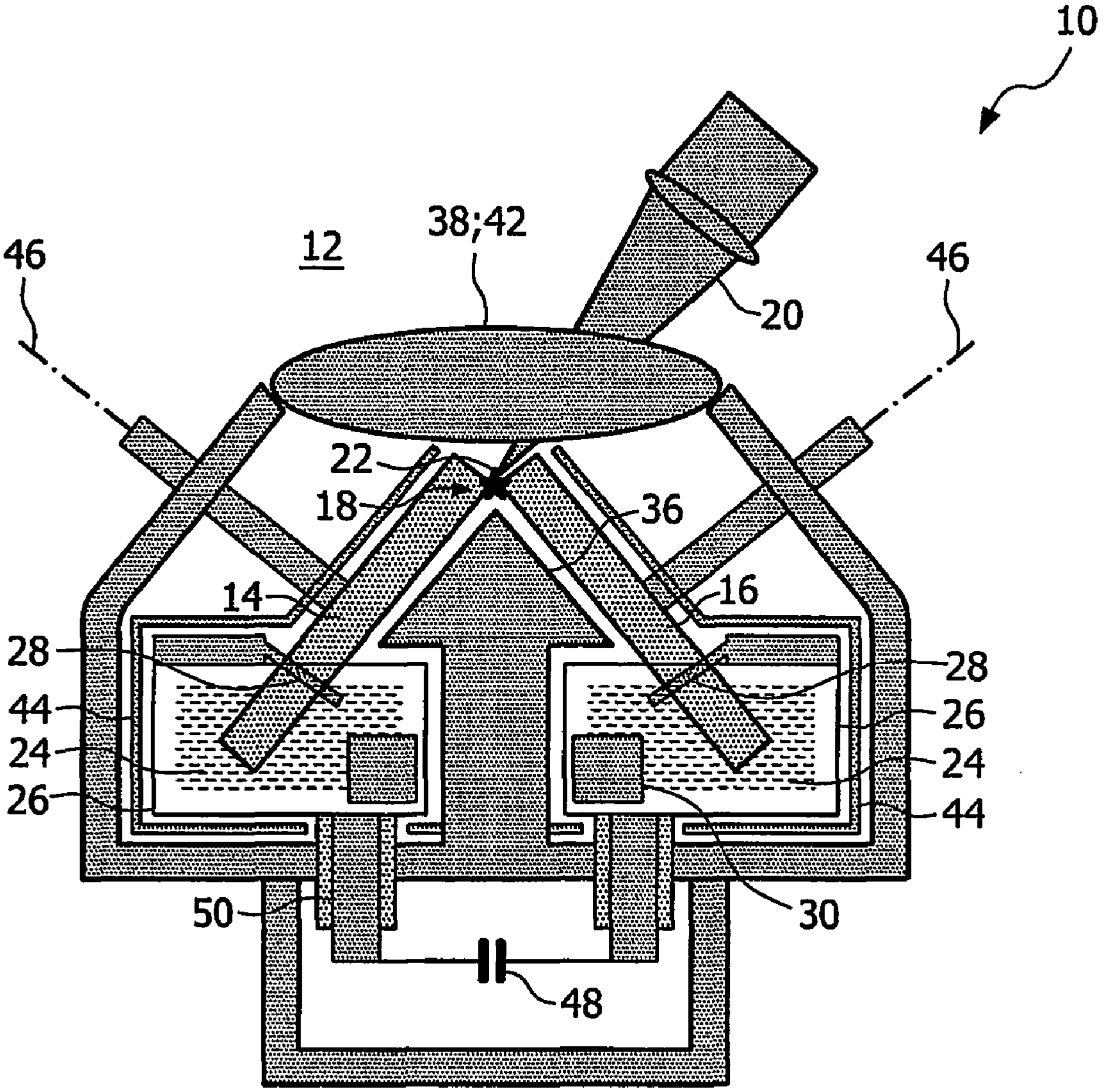
FIG. 1 shows a schematic, partially cut-away side view of the apparatus according to a first embodiment.

As can be seen in FIG. 1, a metal screen 36 is arranged between the electrodes 14,16.

There are furthermore means 38 and 42 which prevent the metal vapor from escaping and hence prevent soiling of important parts. One means is for example a thin walled, honeycomb structure 38 which is shown in different views in FIGS. 2 and 3. This structure 38 is arranged for example in a cone-shaped manner around a source point 40.

A further means consists of thin metal sheets 42 having electric potentials. These are shown schematically in plan view in FIG. 4. A side view of these metal sheets 42 is similar to that side view shown in FIG. 2.

Furthermore, a screen 44 is arranged between the electrodes 14, 16 and the housing.

Herein below, the method of producing EUV radiation and the modes of action of the individual components of the apparatus 10 that have been specified above will be described with reference to FIGS. 1 to 7.

The present invention is therefore a system in which radiation can also be produced using substances which have a high boiling point. Moreover, the system has no rotatable current and fluid cooling ducts.

The description will now be given of one special embodiment of the electrodes 14, 16, the power supply, the cooling and the special provision of the radiating medium, for providing a simple cooling and a greater efficiency of the radiation production.

FIG. 1 shows a diagram of the radiation source according to the invention. The operating electrodes consist of two rotatably mounted disk-shaped electrodes 14, 16. These electrodes 14, 16 are partially dipped into in each case a temperature-controlled bath comprising liquid metal, e.g. tin. In the case of tin, which has a melting point of 230° C., an operating temperature of 300° C. is favorable for example. If the surface of the electrodes 14, 16 can be wetted by the liquid metal or the metal melt 24, when the electrodes are rotated out of the metal melt 24 a liquid metal film forms on said electrodes 14, 16. This process is similar to the production process, for example, when tin-plating wires. The layer thickness of the liquid metal may typically be set within the range of 0.5 μm to 40 μm. This depends on parameters such as temperature, speed of rotation and material properties, but may also be set in a defined manner for example mechanically by a mechanism for stripping off the excess material, for example by means of the strippers 28. As a result, the electrode surface used up by the gas discharge is continuously regenerated, so that advantageously no longer any wear occurs to the base material of the electrodes 14, 16.

A further advantage of the arrangement consists in that an intimate heat contact takes place by the rotation of the electrodes 14, 16 through the metal melt 24. The electrodes 14, 16 heated by the gas discharge can thus give off their energy efficiently to the metal melt 24. The rotating electrodes 14, 16 therefore require no separate cooling, but rather only the metal melt 24 must be kept to the desired temperature by suitable measures.

An additional advantage consists in that there is a very low electrical resistance between the electrodes 14, 16 and the metal melt 24. As a result it is readily possible to transmit very high currents as are necessary, for example, in the case of the gas discharge to produce the very hot plasma 22 suitable for radiation production. In this way, there is no need for a rotating capacitor bank which supplies the current. The current can be fed in a stationary manner via one or more feed lines 50 from outside to the metal melt 24.

Advantageously, the electrodes 14, 16 are arranged in a vacuum system which reaches at least a basic vacuum of $10^{-4}$ mbar. As a result, a higher voltage from the capacitor bank 48 of, for example, 2-10 kV can be applied to the electrodes 14, 16 without leading to an uncontrolled disruptive discharge. This disruptive discharge is triggered by means of a suitable laser pulse. This laser pulse is focused on one of the electrodes 14 or 16 at the narrowest point between the electrodes 14, 16 in the region 18. As a result, part of the metal film located on the electrodes 14, 16 evaporates and bridges over the electrode gap. This leads to the disruptive discharge at this point and to a very high flow of current from the capacitor bank 48. This current heats the metal vapor to such temperatures that the latter is ionized and emits the desired EUV radiation in a pinch plasma.

In order to produce the pinch plasma, pulse energies of typically one Joule to several tens of Joules are converted. A substantial proportion of this energy is concentrated in the pinch plasma, which leads to thermal loading of the electrodes 14, 16. The thermal loading of the electrodes 14, 16 by the pinch plasma is produced by the emission of radiation and of hot particles (ions). Moreover, the discharge current of more than 10 kA must be fed to the gas discharge from the electrodes 14, 16. Even at high electrode temperatures the thermal emission of the cathode is not sufficient to make available enough electrons for this flow of current. The process of cathode spot formation known from vacuum spark discharges starts at the cathode, which heats up the surface in a localized manner such that electrode material evaporates from small areas (cathode spots). From these spots, the electrons for the discharge are made available for periods of a few nanoseconds. Thereafter, the spot is quenched again and the phenomenon is repeated at other points of the electrode 14 or 16 so that a continuous flow of current is produced.

However, this process is often associated with the fact that some of the electrode material is evaporated and condenses at other points of the electrode system. In addition, prior to the gas discharge, the laser pulse likewise leads to energy coupling and to the evaporation of some of the film of melt. The principle proposed here provides an electrode 14, 16 that can be regenerated in that the loaded part of the electrode 14, 16 leaves the region of the flow of current by virtue of the rotation, the surface of the film of melt altered by the discharge automatically becomes smooth again and finally is regenerated again by virtue of the dipping into the liquid metal bath. Moreover, the heat dissipation is considerably assisted by the continuous rotation of the electrodes 14, 16 out of the highly loaded region. It is therefore possible to readily feed electrical powers of several tens of kW into the system and dissipate them again via the metal melt 24.

Advantageously, the electrodes 14, 16 are made of very highly heat conductive material (e.g. copper). They may also be made of copper as a core and be covered by a thin, high-temperature-resistant material (e.g. molybdenum). Such a production is conceivable in that the outer sheath is made, for example, of molybdenum in a thin-walled manner and then is plugged with copper. A heat pipe system is possible as a further measure for efficiently transporting away heat. For instance, in a channel integrated just below the surface there may be a medium which evaporates at the hottest point in the vicinity of the pinch, thereby withdraws heat and condenses again in the colder tin bath. Another embodiment of the electrodes 14, 16 is designed such that in their contour they are not smooth but rather have a profile in order to make available as large a surface as possible in the metal melt 24 or in the tin bath.

The electrodes may also be formed of a porous material (e.g. wolfram). In this case capillary forces are available for transporting the melted material, e.g. tin exhausted by the discharge.

The material of the whole radiation source should be compatible with the melted metal, in particular tin, in order to avoid corrosion. Examples of suitable materials are ceramics, molybdenum, wolfram or stainless steel.

In order that, during the process of producing radiation from metal vapor plasma, which is made available from material of the metal film on the electrodes 14, 16 by laser evaporation, the base material of the electrodes 14, 16 is not damaged, the film thickness should not fall below a defined minimum value. In experiments it has been found that in the focus spot of the laser used for vapor production the material is removed by a few micrometers, and moreover the cathode spots formed even lead to small craters having a diameter and a depth of in each case a few micrometers. Advantageously, the metal film on the electrodes 14, 16 should therefore have a minimum thickness of about 5 μm, which is not a problem using the application process in the bath of melt.

The thickness of the layer likewise plays an important role for the thermal behavior. Tin has, for example, a significantly poorer heat conductivity than copper, from which the electrodes 14, 16 may be made. In the case of a tin layer with the minimum required thickness, therefore, considerably more heat can be dissipated, so that a higher electrical power can be coupled in.

Under unsuitable conditions during laser evaporation, however, much deeper removal may occur in the focus spot. This occurs, for example, when a laser with too high a pulse energy or unsuitable intensity distribution in the focus spot or too high an electrical pulse energy for the gas discharge is used. A laser pulse with 10 mJ to 20 mJ and an electrical energy of 1 to 2 J has proven advantageous, for example. Moreover, it is advantageous if the intensity distribution in the laser pulse is as uniform as possible. In the case of so-called monomode lasers, the intensity distribution has a Gaussian profile and is therefore highly reproducible but has a very high intensity in the center.

In the case of multimode lasers, the intensity in the laser spot may exhibit very pronounced spatial and temporal fluctuation. As a result, this may likewise lead to excessive removal of material. It is particularly advantageous if the laser pulse is firstly transmitted via an optical fiber. By virtue of the many reflections in the fiber, the spatial intensity distribution is leveled out such that a completely uniform intensity distribution in the spot is achieved by focusing by means of a lens system. The metal film is therefore also removed very uniformly over the diameter of the crater produced.

The metal film should also not be applied too thick in order to protect the electrodes 14, 16. Specifically, it has been found in experiments that in the case of a very thick film there is a risk that a large number of metal droplets will be formed by the laser pulse and the subsequent gas discharge. These droplets are accelerated away from the electrodes 14, 16 at great speed and may condense for example on the surfaces of the mirrors required to image the EUV radiation produced. As a result, said mirrors will be unusable after a short time. The metal film is naturally up to 40 μm thick and is therefore in some circumstances thicker than necessary. It can be reduced to the desired thickness for example by means of suitable strippers 28 once the electrodes 14, 16 have been rotated out of the metal melt 24.

In order to ensure long operation of the apparatus 10 or radiation source with connected mirror optics, a situation should be prevented in which even very thin layers of the evaporated metal film material deposit on the surfaces. For this, it is advantageous to adapt all the method parameters such that only as much material as necessary is evaporated. Moreover, a system for suppressing the vapor may be fitted between the electrodes 14, 16 and the mirror 34, said system also being referred to as debris mitigation.

One possibility for this is the arrangement of the semi-spherical, as far as possible thin-walled, honeycomb structure 38, made for example of a high-melting metal, between the source point 40 and the mirror 34. The metal vapor which reaches the walls of the honeycomb structure remains there in an adhering manner and therefore does not reach the mirror 34. One advantageous configuration of the honeycomb structure has, for example, a channel length of the honeycombs of 2-5 cm and a mean honeycomb diameter of 3-10 mm given a wall thickness of 0.1-0.2 mm, cf. FIGS. 2 and 3.

A further improvement may be achieved when the vapor, which consists mainly of charged ions and electrons, is conducted through the electrode arrangement of thin metal sheets 42, to which a voltage of several thousands of Volts is applied. The ions are then subject to an additional force and are deflected onto the electrode surfaces.

Figure 2:
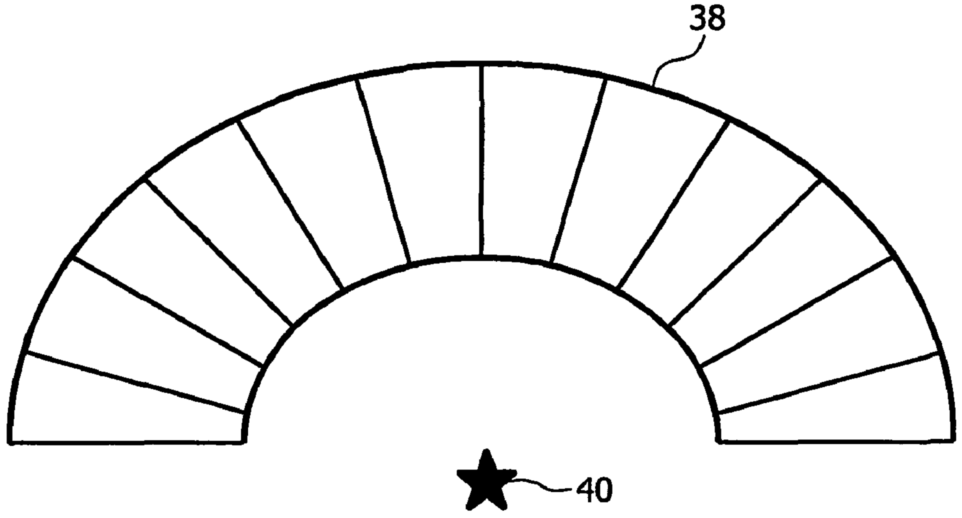
FIG. 2 shows a partially cut-away side view of a first device for debris mitigation.
Figure 3:
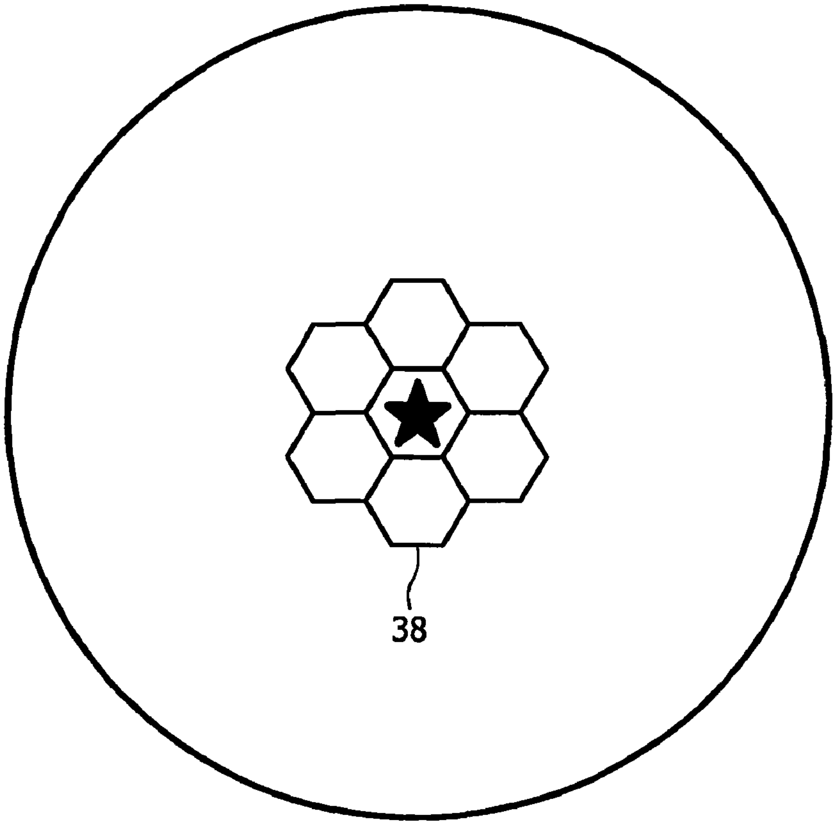
FIG. 3 shows the device shown in FIG. 2 in plan view.
Figure 4:
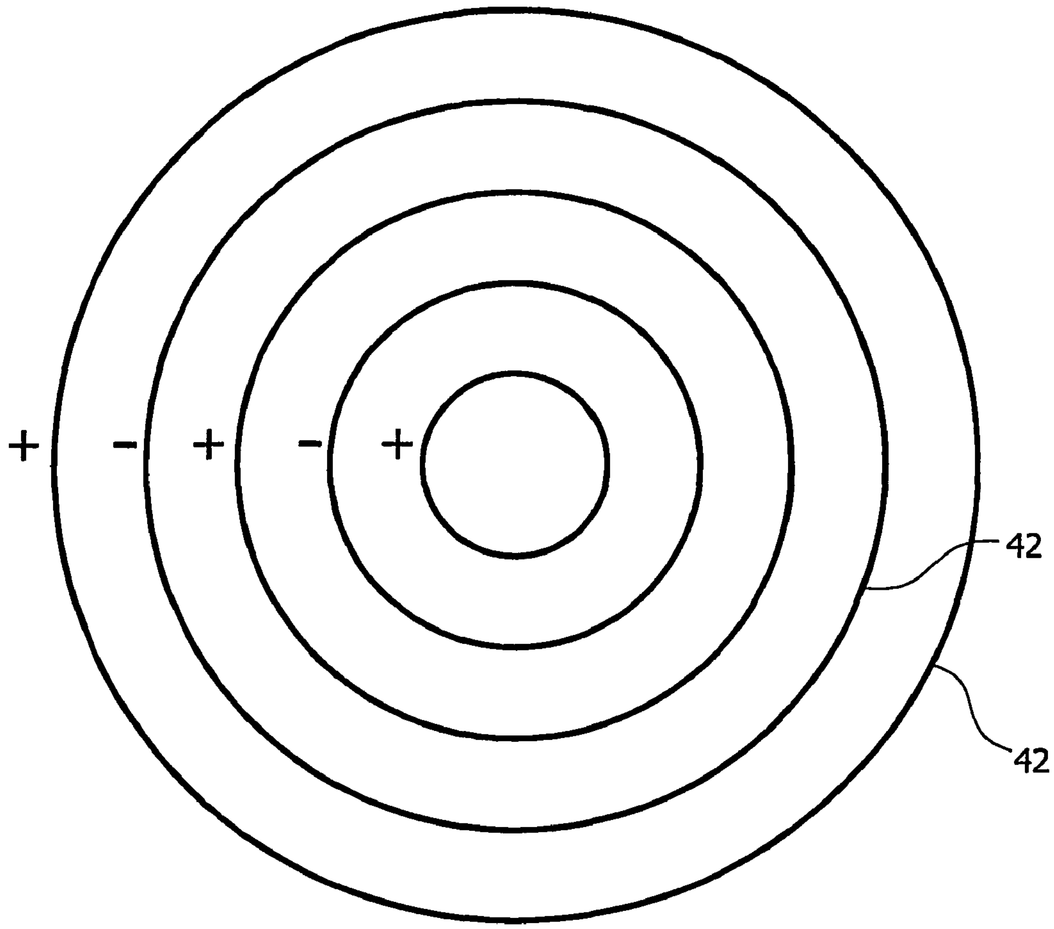
FIG. 4 shows a further device for debris mitigation in plan view, wherein the side view is similar to that of FIG. 2.

One example of a configuration of these electrodes is shown in FIGS. 2 and 4. It is clear that the annular electrode sheets have the shape of an envelope of a cone with the tip in the source point 40, in order that the EUV radiation can pass virtually unhindered through the electrode gaps. This arrangement may also additionally be placed behind the honeycomb structure or replace the latter entirely. There is also the possibility of arranging a number of wire gauzes behind one another between source and collector mirror 34, said wire gauzes being largely transparent to EUV radiation. If a voltage is applied between the gauzes, an electrical field is formed which decelerates the metal vapor ions and deflects them back to the electrodes 14, 16.

A further possibility of preventing the condensation of metal vapor on collector optics consists in placing the two electrodes 14, 16 at a defined potential relative to the housing of the vacuum vessel. This can be done in a particularly simple manner when said electrodes are constructed such that they have no contact with the vacuum vessel. If, for example, the two electrodes 14, 16 are negatively charged with respect to the housing, then positively charged ions, which are emitted by the pinch plasma, are decelerated and pass back to the electrodes 14, 16.

In the event of long operation of the source, it may likewise be damaging if the evaporated metal, such as tin, for example, reaches the walls of the vacuum vessel or the surface of insulators. Advantageously, the electrodes 14, 16 may be provided with the additional screen 44, made for example of sheet metal or even glass, which is provided with an opening only at that point where the radiation is to be coupled out. The vapor condenses on this screen 44 and is passed back into the two tin baths or containers 26 by means of gravity.

This screen 44 can also be used to protect the source from interfering external influences. Such influences can be caused, for example, by the gas present in the collector system. The opening of the screen 44, through which the EUV radiation is emitted to the collector, can serve as an increased pump resistance in order to ensure a low gas pressure in the source region. Furthermore, when buffer gases are used in the source region, the small opening of the screen 44 makes it difficult for these gases to flow to the collector system. Examples for such buffer gases are gases which are highly transparent for EUV radiation or gases with electronegative properties. With these gases a better reconsolidation of the discharge passage can be achieved, the frequency of the radiation source can be increased or the tolerance of the source with respect to gases like e.g. argon, which flow from the collector region to the source region can be increased.

Figure 5:
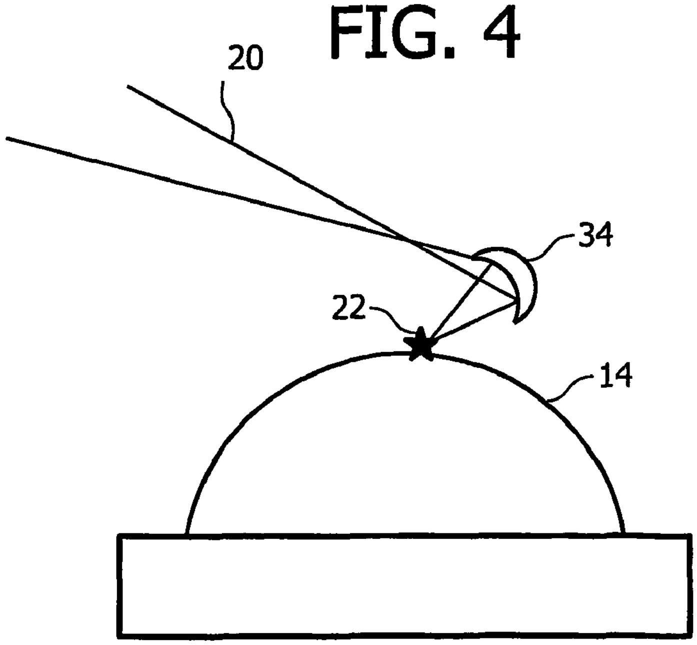
FIG. 5 shows a schematic diagram of the coupling of the laser beam onto the electrode surface.

In the example of the embodiment shown in FIG. 5, for example, the laser beam 20 is conducted by means of a glass fiber (not shown) from the laser device to the beam-forming surface which focuses the pulse onto the surface of one of the electrodes 14, 16. In order not to arrange any lenses in the vicinity of the electrodes 14, 16, which lenses easily would lose their transmission on account of the metal vapor produced, the mirror 34 may be arranged there with a suitable shape. Although metal also evaporates there, the mirror 34 nevertheless does not thereby significantly lose its reflectance for the laser radiation. If this mirror 34 is not cooled, it automatically heats up in the vicinity of the source. If its temperature reaches, for example, more than 1000° C., the metal, e.g. tin, can evaporate completely again between the pulses, so that the original mirror surface is always available again for the new laser pulse.

In some circumstances, it is more favorable for the evaporation process if the laser pulse is not focused onto a single round spot. It may be advantageous to distribute the laser energy for example over a number of points or in a circular manner.

The mirror 34 furthermore has the advantage that it deflects the laser radiation or laser beam 20. It is therefore possible to arrange the remaining optics for coupling in the laser such that the EUV radiation produced is not shaded thereby. In a further embodiment the mirror 34 is placed on the side opposing the side for coupling out the EUV radiation. In this arrangement the EUV radiation produced is not shaded at all by the laser optics.

It is advantageous if the two electrodes 14, 16 with the associated containers 26 or tin baths do not have any electrical contact with the metal vacuum vessel and e.g. the honeycomb structure 38 above the source point 40. They are arranged in a potential-free manner. As a result it is not possible for example for a relatively large part of the discharge current to flow there and remove disruptive dirt in the vacuum system.

By virtue of the potential-free arrangement, moreover, the charging of the capacitor bank 48 can take place in an alternating manner with different voltage directions. If the laser pulse is also accordingly deflected in an alternating manner onto the various electrodes 14, 16, then the latter are loaded uniformly and the electrical power can be increased even further.

In order to generate a peak current that is as high as possible by the metal vapor plasma from the electrical energy stored in the capacitors, the electric circuit should be designed to be of particularly low inductance. For this purpose, for example, the additional metal screen 36 may be arranged as close as possible between the electrodes 14, 16. By virtue of eddy currents during the discharge, no magnetic field can enter the volume of the metal, so that a low inductance results therefrom. Moreover, the metal screen 36 may also be used in order for the condensed metal or tin to flow back into the two containers 26.

In a further embodiment, as schematically indicated in FIG. 9, the metal screen 36 is also rotated and dips, while rotating, into a separate container 56 containing metal melt 24 in order to receive the metal melt 24. The further container 56 is electrically insulated from the containers 26 for the electrodes 14, 16. With this arrangement a direct transport of the debris to the baths as well as a better thermal durability of the metal baths are achieved. Furthermore it is possible to direct the laser beam 20 onto the liquid metal film on the surface of the rotating metal screen 36 in order to produce the metal vapor for the plasma. The power supply to the electrodes in this case is realized in the same manner as described with respect to FIG. 1.

Since, by virtue of the laser and the gas discharge, a power of up to several tens of kW is coupled into the electrodes 14, 16, a large amount of heat accordingly has to be dissipated. For this purpose, for example, the liquid metal (tin) may be conducted in an electrically insulated manner by means of a pump from the vacuum vessel into a heat exchanger and be returned again. In the process, the material lost as a result of the process can be carried back at the same time. Moreover, the metal may be conducted through a filter and be cleaned of oxides, etc. Such pump and filter systems are known, for example, from metal casting.

The heat may of course also be dissipated conventionally by means of cooling coils in the liquid metal or tin or in the walls of the containers 26. In order to assist the dissipation of heat, stirrers which dip into the metal may also be used for more rapid flow.

The gas discharge which produces the plasma pinch and hence the EUV radiation is always produced at the point of the electrodes 14, 16 where the latter are closest together. In the case of the arrangement of the containers 26 and electrodes 14, 16 as shown in FIG. 1, this point is at the top where the laser pulse also strikes, so that in this case the radiation also has to be coupled out vertically upward. In some applications, however, other angles are necessary, e.g. horizontally or oblique upward. These requirements may likewise be implemented using the same principle on which this invention is based.

For this purpose, for example, the rotation axes 46 of the electrodes 14, 16 may be inclined not only upward but also laterally with respect to one another. This means that the smallest distance is no longer at the top but rather migrates downward to a greater or lesser extent depending on the inclination. A further embodiment consists in that the electrodes 14, 16 do not have the same diameter and do not have a simple disk shape, as shown in FIG. 7.

With the convoluted arrangement and design of the electrodes 14, 16 of FIG. 7 intervisibility between the pinch plasma region and the tin baths is avoided. This results in a better thermal screening of the tin baths. Debris from the plasma is picked up by the tin film on the electrodes and transported back to the baths by the rotating electrodes.

It is advantageous if the containers 26 consist of an insulating material, e.g. of quartz or ceramic, which containers are connected directly to a baseplate 54 which likewise consists of quartz or ceramic and is flanged to the vacuum system. The electrical connection of the externally arranged capacitor bank 48 and the liquid metal in the containers 26 may be achieved by means of a number of metal pins 52 or metal bands embedded in a vacuum-tight manner in the insulators. As a result, a particularly low-inductive electrical circuit can be produced since the insulation of the high voltage is particularly simple on account of the large distances to the vacuum vessel. This arrangement may be produced, for example, using the means used in the production of incandescent lamps.

The region 18 in which the electrodes 14, 16 come closest to one another during the rotation and where the ignition of the gas discharge is triggered by the laser pulse is very important for the function of the EUV source. For the sake of simplicity, in FIG. 1, the electrodes 14, 16 are shown externally with a rectangular cross section. As a result, only two sharp edges lie opposite one another, which may cause a too thin metal film thickness and as a result a very quick wear. It is advantageous if these edges are rounded or are even provided with fine grooves. The metal film can adhere particularly well within these grooves and thus protect the base material. However, small cups may also be made, the diameter of which is somewhat greater than the laser spot. In the case of such an embodiment, however, the rotational speed of the electrodes 14, 16 must be synchronized exactly with the laser pulses in order that the laser always strikes a cup.

In general, the electrodes 14, 16 can be designed freely, e.g. disk-shaped or cone-shaped, with the same dimensions or different dimensions or in any desired combination thereof. They can be designed with sharp or rounded edges or with structured edges, for example in the form of grooves and cups.

During operation of the EUV source, the thickness of the tin film should not be altered. This would entail a series of disadvantages such as increased droplet formation, poorer heat conduction to the electrodes 14, 16 or even destruction of the electrodes 14, 16. If the metal film is too thin, the laser pulse or the gas discharge may also remove material from the electrodes 14, 16. This material is ionized and electronically excited both by the laser pulse and by gas discharge, such as the metal, for example tin, and thus likewise radiates electromagnetic radiation. This radiation may be distinguished from the radiation of the metal or tin on account of its wavelength, for example using filters or spectrographs.

If, therefore, a detector (not shown), which consists for example of a spectral filter and a photodetector, is integrated in the EUV source, then either the source may be switched off or the process may be controlled differently. If the metal film is too thick, there is a risk that more vapor and droplets than necessary will be produced. This ionized vapor then also passes into the region of the electrical fields which are produced by the metal sheets 42 shown in FIG. 4 (side view as per FIG. 2), these metal sheets also being referred to here as secondary electrodes, in order to ultimately deflect the vapor and keep it away from the optics. This leads to a flow of current between these secondary electrodes by the ions and electrons. This of course also applies in respect of the above mentioned wire gauzes.

If this current flow is measured, the amount of vapor and the evaporation process can then also be deduced from the amplitude and the temporal distribution of the current signal. As a result, there is also the possibility of controlling the entire process.

LIST OF REFERENCE SIGNS

10 apparatus
12 discharge space
14 1st electrode
16 2nd electrode
18 region
20 laser beam
22 plasma
24 metal melt
26 device, container
28 device, stripper
30 means, heating device, cooling device
34 mirror
36 metal screen
38 structure
40 source point
42 metal sheet
44 screen
46 rotation axis
48 capacitor bank
50 feed line
52 metal pin
54 baseplate
56 separate container

The invention claimed is:

1. A method of producing extreme ultraviolet radiation (EUV) or soft X-ray radiation by means of an electrical operated discharge, in particular for EUV lithography or for metrology, in which a plasma (22) is ignited in a gaseous medium between at least two electrodes (14, 16) in a discharge space (12), said plasma emitting said radiation that is to be produced, wherein said gaseous medium is produced from a metal melt (24), which is applied to a surface in said discharge space (12) and at least partially evaporated by an energy beam, in particular by a laser beam (20).

2. A method as claimed in claim 1, wherein said metal melt (24) is applied to a surface of said two electrodes (14, 16) and/or to a surface of a metal screen (36) arranged between said two electrodes (14, 16).

3. A method as claimed in claim 2, wherein said electrodes (14, 16) and/or said metal screen (36) are placed in rotation during operation.

4. A method as claimed in claim 3, wherein said electrodes (14, 16) are placed in rotation around rotation axes, which are inclined to each other.

5. A method as claimed in claim 3, wherein said electrodes (14, 16) and/or said metal screen (36) dip, while rotating, into containers (26, 56) containing the metal melt (24) in order to receive the metal melt (24).

6. A method as claimed in claim 5, wherein said electrodes (14, 16) are supplied with power via the metal melt (24).

7. A method as claimed in claim 2, wherein said metal melt (24) is evaporated on at least one of the surfaces of said two electrodes (14, 16) by said energy beam (20).

8. A method as claimed in claim 2, wherein said metal melt (24) is evaporated on the surface of said metal screen (36) by said energy beam (20).

9. A method as claimed in claim 1, wherein the energy beam (20) is a laser beam (20) which is transmitted by a glass fiber.

10. A method as claimed in claim 1, wherein the energy beam (20) is distributed over a number of points or a circular ring on said surface for evaporation of said metal melt (24).

11. A method as claimed in claim 1, wherein the radiation produced is detected by means of a detector, the output value of which controls or switches off the production of said radiation.

12. An apparatus (10) for producing extreme ultraviolet radiation (EUV) or soft X-ray radiation by means of an electrically operated discharge, in particular for EUV lithography or for metrology, comprising at least two electrodes (14, 16)

arranged in a discharge space (12) at a distance from one another which allows ignition of a plasma in a gaseous medium between said electrodes, wherein said apparatus further comprises a device (26, 56) for applying a metal melt (24) to a surface in said discharge space (12) and an energy beam device adapted to direct onto said surface an energy beam (20) evaporating said applied metal melt (24) at least partially thereby producing said gaseous medium.

13. An apparatus as claimed in claim 12, wherein said device (26, 56) is adapted for applying the metal melt (24) to a surface of said electrodes (14, 16) and/or to a surface of a metal screen (36) arranged between said two electrodes (14, 16).

14. An apparatus as claimed in claim 13, wherein said electrodes (14, 16) and/or said metal screen (24) can be placed in rotation during operation.

15. An apparatus as claimed in claim 14, wherein said electrodes (14, 16) can be placed in rotation around rotation axes, which are inclined to each other.

16. An apparatus as claimed in claim 14, wherein said electrodes (14, 16) and/or said metal screen (36) dip, while rotating, into containers (26, 56) containing the metal melt (24) in order to receive the metal melt (24).

17. An apparatus as claimed in claim 16, wherein the electrodes (14, 16) are electrically connected to a power supply via the metal melt (24).

18. An apparatus as claimed in claim 16, further comprising a device (28) for setting a layer thickness of the metal melt (24) applied to the two electrodes (14, 16) and/or the metal screen (36).

19. An apparatus as claimed in claim 18, wherein said device for setting a layer thickness is a stripper (28) that reaches up to an outer edge of the respective electrodes (14, 16) and/or the metal screen (36).

20. An apparatus as claimed in claim 12, wherein the electrodes (14, 16) have at least one core of highly heat-conductive material.

21. An apparatus as claimed in claim 12, wherein the electrodes (14, 16) have at least one copper core which is provided with a high-temperature-resistant sheath.

22. An apparatus as claimed in claim 12, further comprising means (38; 42) which prevent metal vapor from escaping.

23. An apparatus as claimed in claim 22, wherein said means are formed by a thin-walled honeycomb structure (38) and/or thin metal sheets (42) having electric potentials and/or wire gauzes having electric potentials.

24. An apparatus as claimed in claim 12, wherein the energy beam device is a laser beam device comprising a glass fiber for transmitting said laser beam (20).

25. An apparatus as claimed in claim 12, wherein means for distributing the energy beam (20) over a number of points or over a circular ring on said surface for evaporating said applied metal melt (24) are provided.

26. An apparatus as claimed in claim 12, wherein a metal screen (36) is arranged between the electrodes (14, 16).

* * * * *